(12) United States Patent
Lee et al.

(10) Patent No.: US 7,491,528 B2
(45) Date of Patent: Feb. 17, 2009

(54) **METHOD FOR EXTRACELLULAR PRODUCTION OF TARGET PROTEINS EMPLOYING OMPF IN *E. COLI***

(75) Inventors: Sang-Yup Lee, Taejon (KR); Ki-Jun Jeong, Taejon (KR)

(73) Assignee: Korea Advanced Institute of Science and Technology (KR)

( * ) Notice: Subject to any disclaimer, the term of this patent is extended or adjusted under 35 U.S.C. 154(b) by 478 days.

(21) Appl. No.: 10/600,145

(22) Filed: Jun. 19, 2003

(65) Prior Publication Data
US 2005/0019857 A1      Jan. 27, 2005

Related U.S. Application Data

(63) Continuation of application No. PCT/KR02/01547, filed on Aug. 13, 2002.

(30) Foreign Application Priority Data

Aug. 14, 2001    (KR) .................. 10-2001-0048881

(51) Int. Cl.
| | |
|---|---|
| C12P 21/06 | (2006.01) |
| C12P 21/04 | (2006.01) |
| C12N 15/64 | (2006.01) |
| C12N 1/20 | (2006.01) |
| C12N 15/00 | (2006.01) |
| C12N 15/09 | (2006.01) |
| C12N 15/63 | (2006.01) |
| C12N 15/70 | (2006.01) |
| C12N 15/74 | (2006.01) |

(52) U.S. Cl. .................. 435/320.1; 435/69.1; 435/69.7; 435/71.1; 435/71.2; 435/91.4; 435/252.3; 435/252.33; 435/471; 435/476

(58) Field of Classification Search ........................ None
See application file for complete search history.

(56) References Cited

U.S. PATENT DOCUMENTS

| | | | | |
|---|---|---|---|---|
| 5,658,757 | A * | 8/1997 | Haake et al. ................ | 435/69.1 |
| 5,840,518 | A * | 11/1998 | Morishita et al. ........... | 435/69.1 |
| 6,274,345 | B1 * | 8/2001 | Lee et al. .................... | 435/69.7 |
| 7,070,989 | B2 * | 7/2006 | Lee et al. ................. | 435/320.1 |
| 7,186,525 | B2 * | 3/2007 | Sakanyan et al. ........... | 435/69.1 |
| 2005/0019857 | A1* | 1/2005 | Lee et al. .................... | 435/69.1 |
| 2005/0207977 | A1* | 9/2005 | Reinl et al. ................. | 424/1.49 |
| 2006/0218667 | A1* | 9/2006 | Vojdani et al. .............. | 800/280 |

FOREIGN PATENT DOCUMENTS

| | | | |
|---|---|---|---|
| WO | WO 87/06953 | A1 * | 11/1987 |
| WO | WO 94/25592 | A2 * | 11/1994 |
| WO | WO 97/26359 | A1 * | 7/1997 |
| WO | WO 03/016538 | A1 * | 2/2003 |
| WO | WO 2005/123924 | A1 * | 12/2005 |

OTHER PUBLICATIONS

Park et al, Biotechnol. Prog., 1999, 15:164-167.*
Makrides, Microbiological Reviews, Sep. 1996, 60/3:512-538.*
Kitai et al, Appl. Microbiol. Biotechnol., 1988, 28:52-56.*
Elfassi et al, PNAS, Apr. 1986, 83:2219-2222.*
Kim et al, Biotechnology Letters, Aug. 1998, 20/8:799-803.*
Kleman et al, Current Biology, 1994, 5:180-186.*
Hellmuth et al, J. Biotechnology, 1994, 32:289-298.*
Nagahari et al, EMBO Journal, 1985, 4/13A:3589-3592.*
Lee, Trends in Biotechnol., Mar. 1996, 14:98-105.*
Kern et al, Gene, 1995, 163:53-57.*
Yoon et al, Biotechnology and Bioengineering, Mar. 30, 2003, 81/7:753-767.*
Jeong et al, Applied and Environmental Microbiology, Jul. 1999, 65/7:3027-3032.*
Jeong et al, Applied and Environmental Microbiology, Oct. 2002, 68/10:4979-4985.*
Simula et al, Toxicology, Oct. 5, 1993, 82/1-3:3-20 abstract only.*
Hahn et al, FEMS Immunology and Medical Microbiology, 1998, 20:111-119.*
Weinstock et al, PNAS, USA, Jul. 1983, 80:4432-4436.*
Lawrence et al, Infection and Immunity, Apr. 1990, 58/4:970-977.*
Inokuchi et al, Nucleic Acid Research, 1982, 10/21:6957-6968.*
Hoffman et al, PNAS, USA, Aug. 1985, 82:5107-5111.*
Choi et al, Chemical Ingineering Science, 2006, 61:876-885.*
Shibui, et al., High-level secretion of human Apolipoprotein E Produced in *Escherichia coli*: use of a secretion plasmid containing tandemly polymerized ompF-hybrid gene., 1991, Journal of Biotechnology, 17 109-120.
Shibui, et al., Secretion of a fuctional Fab fragment in *Escherichia coli* and the influence of culture conditions., 1992, Applied Microbiology Biotechnology, 37: 352-357.

* cited by examiner

*Primary Examiner*—N. M Minnifield
(74) *Attorney, Agent, or Firm*—Knobbe Martens Olson & Bear LLP

(57) ABSTRACT

The present invention provides an expression vector comprising genes encoding OmpF of *E. coli* and a desired protein, *E.coli* transformed with the expression vector, and a method for extracellular production of desired proteins by employing the same. The recombinant expression vector of the invention comprises an ampicillin-resistance gene, the OmpF promoter and the OmpF gene. In accordance with the invention, a desired protein can be produced extracellularly by a simpler method than conventional methods such that: secretory production of OmpF fusion protein begins simultaneously with growth of the cells through constitutive expression employing an OmpF promoter, and as the concentration of cells increases, the amount of secretory production of the protein also increases continuously. Therefore, desired proteins can be produced in large quantities by a high concentration culture of cells.

26 Claims, 4 Drawing Sheets

METHOD FOR EXTRACELLULAR PRODUCTION OF TARGET PROTEINS EMPLOYING OMPF IN E. COLI

This application is a Continuation of International Application PCT/KR02/01547, filed Aug. 13, 2002, which claims priority of Korean Provisional application KR 2001/48881, filed Aug. 14, 2001.

FIELD OF THE INVENTION

The present invention relates to a method for extracellular production of desired proteins employing outer membrane protein F(OmpF) of Escherichia coli(E. coli), more specifically, the present invention relates to an expression vector comprising genes encoding OmpF and a desired protein, E. coli transformed with the expression vector, and a method for the extracellular production of desired proteins by employing the same.

BACKGROUND OF THE INVENTION

It is known that extracellular production of desired foreign proteins in E. coli is a very efficient method in the sense that: the secreted foreign proteins are protected against proteolysis by proteolytic enzymes in E. coli, the secretion process guides appropriate folding of foreign proteins to inhibit the formation of insoluble inclusion bodies, and the N-terminal secretion signal peptide is removed from foreign proteins during the secretion process to keep the amino acid sequence identical to the naturally occurring one. This method also allows mass production of foreign proteins through high concentration culture and continuous culture. Furthermore, this method makes for pure purification of foreign proteins because little bacterial proteins are secreted into culture media.

Since the extracellular production has several advantages as mentioned above, various studies on the extracellular production systems have been actively pursued to produce desired foreign proteins in E. coli. The extracellular production systems developed so far are classified in the following three categories: the first one is a method for extracellular production by the recombination of a secretion signal sequence and a desired foreign protein. For example, Toksoy et al. produced TaqI protein on the cell surface employing a fusion protein containing a secretion signal sequence and maltose binding protein(MBP), Lo et al. produced β-1,4-endoglucanase of Bacillus subtilis on the cell surface of E. coli, and Nagahari et al. produced β-endorphine on the cell surface of E. coli through the recombination of the OmpF secretion signal peptide and 8 amino acids from the N-terminus of OmpF. In addition, Yamamoto et al. tried to produce p21 protein from harvey murine sarcoma virus extracellularly by using the OmpF secretion signal sequence. However, it turned out that p21 was not produced on the cell surface, but accumulated in inclusion bodies(see: Toksoy E. et al., Biotechnology Techniques, 13:803-808, 1999; Lo A. C. et al., Appl. Environ. Micrbiol., 54:2287-2292, 1988; Nagahari et al., EMBO J., 4:3589-3592, 1985; and, Yamamoto et al., Appl. Micobiol. Biotechnol., 35:615-621, 1991).

The second classification is a method for extracellular production by the recombination of a secretion protein from E. coli and a desired protein. For example, Baneyx et al. produced OmpA-TEM-β-lactamase fusion protein on the cell surface together with TolAIII membrane protein of E. coli, Robbens et al. used kil gene to produce interleukin-2, van der Wal et al. used a lipoprotein, BRP(bacteriocin release protein), to produce β-lactamase on the cell surface, and Aristidou et al. increased the yield of extracellular production using BRP by addition of glycine to culture media(see: Baneyx F. and Eugene W. M., Protein Expr. Purif., 14:13-22, 1998; Robbens J. et al., Protein Expr. Purif., 6:481-486, 1995; van der Wal F. J. et al., Appl. Environ. Microbiol., 64:392-398, 1998; and, Aristidou A. A. et al., Biotechnol. Lett., 15:331-336, 1993).

The third classification is a method for extracellular production by the aid of an outer membrane-free E. coli, such as an L-type strain of E. coli, a mutant that has only an inner cellular membrane without an outer cellular membrane and periplasm. The extracellular production of foreign proteins is simpler than prior methods in the culture of an L-type strain because expressed proteins are transported through only the inner cellular membrane to be secreted into culture media. For example, Kujau et al. used RV308 strain, an L-type mutant, to produce a miniantibody(miniAb) on the cell surface(see: Kajau M. J. et al., Appl. Microbiol. Biotechnol., 49:51-58, 1998).

As expounded above, a variety of methods have been developed to produce desired foreign proteins on the cell surface of E. coli. Most of these prior art methods are, however, proven to be less satisfactory because partial degradation of some foreign proteins by bacterial proteolytic enzymes makes the purification process complex and makes high concentration cell culture impossible. In addition, extracellular production employing an L-type strain of E. coli has shortcomings in that the said strain is not suitable for high concentration cell culture due to its weak resistance to environmental stress and its short life cycle.

Under the circumstances, there are strong reasons for exploring and developing an alternative method for extracellular production of desired foreign proteins on the cell surface of E. coli.

SUMMARY OF THE INVENTION

A novel method for extracellular production of desired foreign proteins on the cell surface of E. coli was developed herein. During the development, it was found that fusion proteins could be secreted efficiently into the culture media of recombinant E. coli. The method involves using an E. coli transformed with an expression vector comprising genes encoding the outer membrane protein F(OmpF) of E. coli and a desired protein. Further, it was found that the foreign proteins could be purified in a simple manner by removing OmpF from the fusion proteins.

One aspect is, therefore, to provide an expression vector comprising genes encoding all or a fragment of the OmpF of E. Coli and a desired foreign protein. Preferably, the fragment includes the signal protein from OmpF. The expression vector further comprises a cleavage site separating the OmpF fragment from the gene of interest. Thus, the expression vector provides a fusion protein of the OmpF fragment with the gene of interest, separated by the cleavage site. The expression vector may also include a selectable marker, such as ampicillin resistance. The cleavage site may be an RNase or protease cleavage site. The cleavage site may be any type of cleavage site known to one of skill in the art, including, but not limited to: Factor Xa, enterokinase, IgA protease, intein, genenase, thrombin, trypsin, pepsin, subtilisin, and plasmin. One example of such an expression vector is pOmpF6 deposited as E. coli BL101/pOmpF6 deposited with the Korean type culture Collection for Type cultures under accession number KCTC 1026BP.

A further aspect is to provide a microorganism that is transformed with the expression vector. In one embodiment, the host microorganism is *E. coli* or *Salmonella* sp. In a further embodiment, the host microorganism lacks the OmpF gene. One example of such a microorganism is *E. coli* BL101/pOmpF6 deposited with the Korean type culture Collection for Type cultures under accession number KCTC 1026BP.

Another aspect is a method for extracellular production of a desired protein by culturing the transformed microorganism. The protein, which is highly over-expressed, can then be purified by removing the cellular material, purifying the OmpF fusion protein from the media, cleaving the OmpF portion using an enzyme appropriate for the cleavage site, and isolating the protein of interest. One method of purifying the OmpF fusion protein is by using anion-exchange chromatography and/or reverse-phase HPLC.

BRIEF DESCRIPTION OF THE DRAWINGS

The above objects and features of the present invention will become apparent from the following descriptions given in conjunction with the accompanying drawings, in which.

DETAILED DESCRIPTION OF THE PREFERRED EMBODIMENTS

Figure 1:
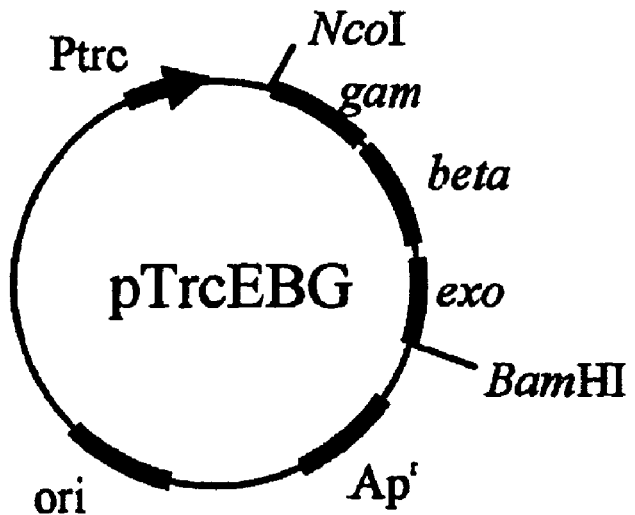
FIG. 1 represents a genetic map of the recombinant expression vector pTrcEBG.

One embodiment of an expression vector of the present invention contains an OmpF promoter and part or all of the OmpF gene. A method for extracellular production of a desired protein employs an expression vector comprises a gene encoding an oligopeptide which is recognised and cleaved by a proteolytic enzyme and a gene encoding a desired protein introduced into the expression vector pOmpF6 to construct a recombinant expression vector that produces the desired protein extracellularly. This or an equivalent expression vector is then transformed into a host microorganism lacking the OmpF gene to obtain a transformed microorganism. The transformed microorganism is then cultured and produces an OmpF-fused protein from the culture. Lastly, the fused protein is treated with a proteolytic enzyme and the desired protein obtained. Available proteolytic enzymes include, but are not limited to: Factor Xa, enterokinase (Asp-Asp-Asp-Asp-Lys, SEQ ID NO: 19), genenase(His-Tyr or Tyr-His), IgA Protease (Pro/Ser-Arg/Thr-Pro-Pro-Thr/Ser/Ala-Pro, SEQ ID NO: 20), intein, thrombin, trypsin, pepsin and subtilisin or plasmin, preferably Factor Xa. Available desired proteins include, but are not limited to: peptides, enzymes and antibodies that can be fused to OmpF, preferably β-endorphin. Microorganisms can be *Escherichia* sp. or *Salmonella* sp., but are not limited to these preferred host microorganisms.

The present inventors cultured six *E. coli* strains (BL21 (DE3), HB101, JM101, MC4100, XL1-Blue and W3110), analysed the outer membrane proteins separated from each culture by SDS-PAGE, and found that OmpF protein was over expressed in BL21(DE3) strain. The present inventors constructed an expression vector pOmpF6, which consists of OmpF gene of *E. coli*, OmpF promoter, and an ampicillin resistance gene. OmpF gene and OmpF promoter were cloned by performing PCR using genomic DNA isolated from BL21 (DE3) as a template and specific primers. *E. coli* BL101 strain was transformed with the said expression vector and the transformant was designated as *E. coli* BL101/pOmpF6(*Escherichia coli* BL101/pOmpF6) and deposited with the Korean Collection for Type Cultures(KCTC, #52 Oun-dong, Yusong-ku, Taejon 305-333, Republic of Korea), an international depository authority, as Accession No. KCTC 1026BP on Jun. 1, 2001.

Then, the present inventors constructed a recombinant expression vector pOmpF6βE to demonstrate an example of extracellular production of fusion proteins using the expression vector pOmpF6. The recombinant expression vector contains a cDNA encoding β-endorphin, a gene encoding OmpF protein, OmpF promoter, a gene encoding oligopeptide for the recognition and cleavage by Factor Xa, which is inserted between OmpF protein and β-endorphin, and ampicillin resistant gene. The present inventors transformed *E. coli* BL21(DE3) strain(Novagen Co., U.S.A.) with the said recombinant expression vector pOmpF6βE, cultured the said recombinant *E. coli* strain to produce OmpF-β-endorphin fusion proteins on the cell surface, and harvested fusion proteins from culture media. The said harvested fusion proteins were first purified by the anion-exchange chromatography and β-endorphin proteins were recovered after removing OmpF proteins from fusion proteins by Factor Xa.

High concentration cell culture is practically impossible in the conventional cell surface display systems since fusion proteins are degraded by proteolytic enzymes of *E. coli*. In accordance with the invention, a desired protein can be produced extracellularly by a simpler method than conventional methods such that: secretory production of OmpF fusion protein begins simultaneously with growth of the cells through constitutive expression employing the OmpF promoter, and as the concentration of cells increases, the amount of secretory production of the protein also increases continuously. Therefore, desired proteins can be produced in large quantities by a high concentration culture of cells.

The present invention is further illustrated in the following examples, which should not be taken to limit the scope of the invention.

EXAMPLE 1

Selection of *E. coli* Strain Over Expressing OmpF

Six *E. coli* strains conventionally used for the production of recombinant proteins were selected, and outer membrane proteins were purified therefrom and compared with one another by carrying out SDS-PAGE. Six *E. coli* strains thus selected were *E. coli* BL21(DE3)[F-ompT hsdSB(rB-mB-) gal dcm(DE3) a prophage carrying the T7 RNA polymerase gene](Novagen Co., U.S.A.), HB101[F-hsd20(rk-, mk-) recA13 ara-14 proA2 lacY1 galK2 rpsL20(str) xyl1-5 mtl-1 supE44 λ-](New England Biolabs, U.S.A.), JM101[supE thii-1 Δ(lac-proAB) [F'traD36 proAB lacIqZ ΔM15]](Stratagene Co., U.S.A.), MC4100[F-araD139 Δ(argF-lac)U169 rpsL150(strr) relA1 flbB5301 deoC1 ptsF25 rbsR](Stratagene Co., U.S.A.), XL1-Blue[SupE44 hsdR17 recA1 endA1 gyrA96 thi relA1 lacF(proAB+lacIq lacZM15 Tn10(tetr)] (Stratagene Co., U.S.A.), and W3110[derived from K-12, λ-, F—, prototrophic](KCTC 2223). Each of E. coli strains was cultured in 50 mL of LB media(tryptone 10 g/L, yeast extract 5 g/L, NaCl 5 g/L) at 37° C.

Bacterial cells were harvested from each of the cultures and the outer membrane proteins were fractionated by the following process: Bacterial cells were first harvested by centrifuging 3 mL of the culture at 3500×g for 5 min at 4° C. The harvested bacterial cells were washed with 1 mL of $Na_2HPO_4$ (pH 7.2) buffer solution, centrifuged again at 3500×g for 5 min at 4° C., and suspended in 0.5 mL of $Na_2HPO_4$(pH 7.2) buffer solution. The bacterial cell suspension was treated by sonication and centrifuged at 10,000×g for 2 min at room temperature to remove the cell debris. The supernatant was centrifuged at 10,000×g for 30 min at room temperature and the pellet was suspended in 0.5 mL of 10M $Na_2HPO_4$(pH 7.2) buffer solution containing 0.5% (w/v) sarcosyl to prepare the fraction of the outer membrane proteins.

The fraction was incubated at 37° C. for 30 min and centrifuged at 10,000×g for 30 min at 4° C. The pellet was washed with 10 mM $Na_2HPO_4$(pH 7.2) buffer solution and suspended in 50 µl of PBS(0.247M NaCl, 0.041M $Na_2HPO_4$, 0.047M $KH_2PO_4$, 0.005M KCl, pH 7.4) to prepare the fraction sample of the outer membrane proteins for the protein analysis(see: Puenete, J. L. et al., Gene, 156:1-9, 1995). Each of fraction samples was analysed by SDS-PAGE, showing that E. coli BL21(DE3) strain produced a large amount of OmpF protein.

EXAMPLE 2

Preparation of E. coli Strain Lacking an OmpF Gene ompF gene of E. coli BL21(DE3) was deleted by using red operon(exo-beta-gam) of bacteriophage: First, PCR was performed by employing bacteriophage DNA as a template and primer pair of primer 1: 5'-CGCGCCATGGATATTAATACT-GAAACTGAGATCAAGC-3'(SEQ ID NO. 1) and primer 2: 5'-CGGGATCCTCATCGCCATTGCTCCCCAAATAC-3' (SEQ ID NO. 2). The amplified PCR product was separated on 1.2% agarose gel by electrophoresis to obtain 2.2 kb DNA fragment. The DNA fragment was digested with NcoI and BamHI restriction enzymes. The expression plasmid pTrc99A(Pharmacia Biotech Co., U.S.A.) containing trc promoter was also digested with NcoI and BamHI restriction enzymes, and ligated to the PCR product digested with the same restriction enzymes to construct a recombinant expression vector pTrcEBG. Then, E. coli XL1-Blue strain was transformed with the expression vector pTrcEBG and transformants were screened on LB plate containing 50 µg/L ampicillin(see: FIG. 1). FIG. 1 represents a genetic map of recombinant expression vector pTrcEBG. E. coli BL21(DE3) strain was transformed with the recombinant expression vector pTrcEBG and transformants were screened on LB plate containing 50 µg/L ampicillin. The transformant was cultured in 500 mL of LB media until $O.D._{600}$ reached to 0.3 and IPTG(final concentration 1 mM) was added into media to induce the expression of exo-beta-gam gene. After culture for 1 hr, bacterial cells were harvested by centrifugation and washed with 250 mL of deionized distilled water. The harvested cells were suspended in 10 mL of 10% (w/v) glycerol and stored at −80° C. after centrifugation.

Figure 2:
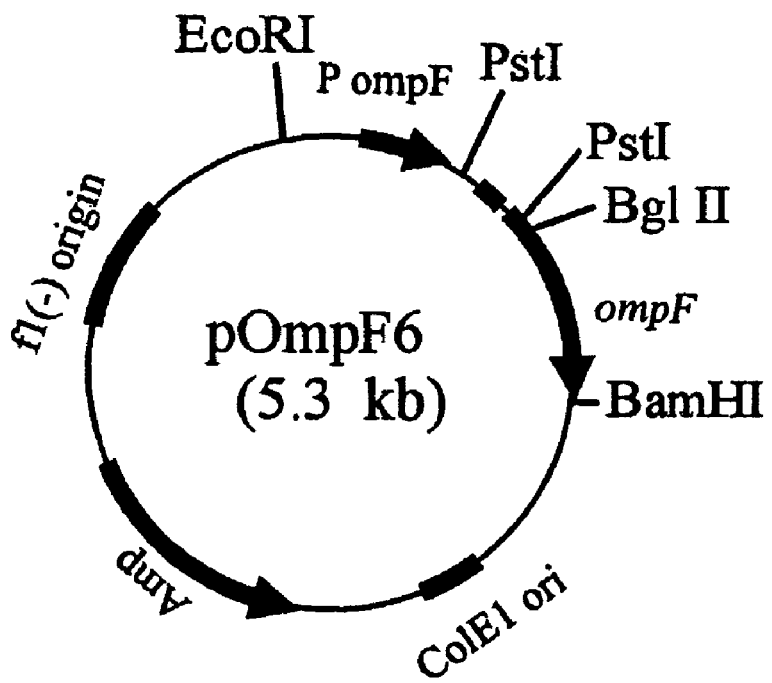
FIG. 2 represents a genetic map of the expression vector pOmpF6.
Figure 3:
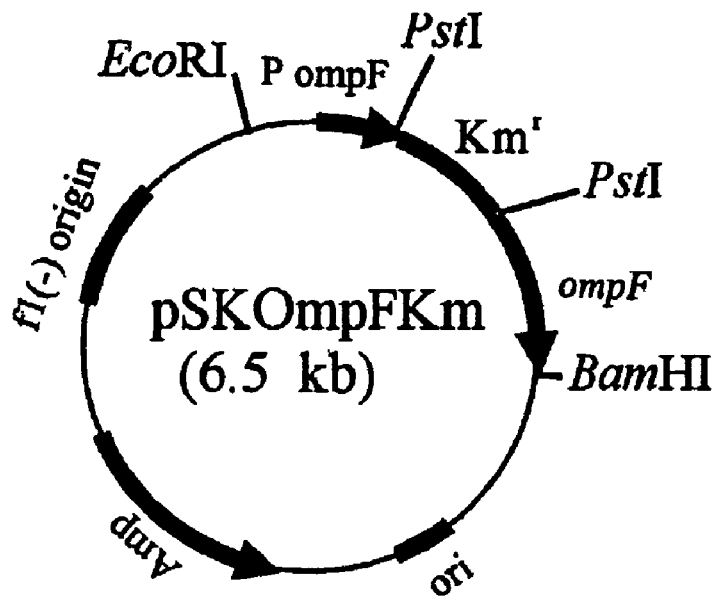
FIG. 3 represents a genetic map of the recombinant expression vector pSKOmpFKm.

On the other hand, PCR was performed using genomic DNA of E. coli BL21(DE3) strain as a template and primer pair of primer 3: 5'-CGGAATTCTGGATTATACCGACG-CAG-3'(SEQ ID NO. 3) and primer 4: 5'-GCGGATCCTTA-GAACTGGTAAACGATAC-3'(SEQ ID NO. 4) to obtain 2,160 bp DNA fragment. The DNA fragment was digested with EcoRI and BamHI restriction enzymes and inserted into pBluescript SK(-)(Stratagene Cloning Systems, U.S.A.) to construct an expression vector pOmpF6. Then, E. coli XL1-Blue strain was transformed with the expression vector, and then transformants were screened on LB plate containing 50 µg/L ampicillin(see: FIG. 2). FIG. 2 represents a genetic map of expression vector pOmpF6. In addition, PCR was performed using an expression vector pACY177(New England Biolabs, U.S.A.) as a template and primer 5: 5'-CGCTG-CAGTTAGAAAAACTCATCGAGCATC-3'(SEQ ID NO. 5) and primer 6: 5'-GCCTGCAGGCCACGTTGTGTCCT-CAAA-3'(SEQ ID NO. 6) to obtain 940 bp DNA fragment. The DNA fragment was digested with PstI restriction enzyme and ligated into PstI-digested plasmid pOmpF6 to construct a recombinant expression vector pSKOmpFKm. Then, E. coli XL1-Blue strain was transformed with the recombinant expression vector pSKOmpFKm, and then the recombinant expression vector pSKOmpFKm containing kanamycin resistant gene was obtained therefrom(see: FIG. 3). FIG. 3 represents a genetic map of recombinant expression vector pSKOmpFKm. As shown in FIG. 3, the recombinant expression vector pSKOmpFKm contains ompF gene and promoter, which are derived from E. coli BL21(DE3) strain, and, kanamycin resistant gene is inserted between ompF promoter and 5'-terminal of ompF gene, by which ompF gene is not expressed. PCR was performed using the recombinant expression vector pSKOmpFKm as a template and primer 3 and primer 4 to obtain DNA fragment comprising ompF gene, its promoter and kanamycin resistant gene inserted between them. The DNA fragment was introduced to E. coli BL21 (DE3) strain transformed with pTrcEBG and transformants were screened on LB plate containing ampicillin and kanamycin. In order to remove expression vector pTrcEBG from the transformants, the transformants was subcultured in LB media five-times for 2 days, and then spread and incubated onto an LB plate containing kanamycin to screen the transformants out which did not grow on the plate. Genomic DNA of the said selected E. coli strain was purified to confirm whether kanamycin resistant gene was inserted between ompF promoter and ompF gene: i.e., PCR was performed using the purified genomic DNA as a template and primer pair of primer 3 and primer 8: 5'-GATCGGAAT-TGATTTGAGTTTCC-3'(SEQ ID NO. 8), and amplified DNA fragment was sequenced. Then, PCR was performed using the purified genomic DNA as a template and primer pair of primer 7: 5'-CCACAGCAACGGTGTCGTCTG-3'(SEQ ID NO. 7) and primer 9: 5'-ATCTTTATCTTTGTAG-CACTTTCAC-3'(SEQ ID NO. 9), and amplified DNA fragment was sequenced. Sequencing of both DNA fragments revealed that kanamycin resistant gene was located between ompF promoter and ompF gene. The said transformed strain was designated as "E. coli BL101".

EXAMPLE 3

Development of Expression System of ompF Gene

In order to express OmpF protein in E. coli BL101 recombinant strain prepared in Example 2, three recombinant expression vectors were constructed, respectively.

Figure 4:
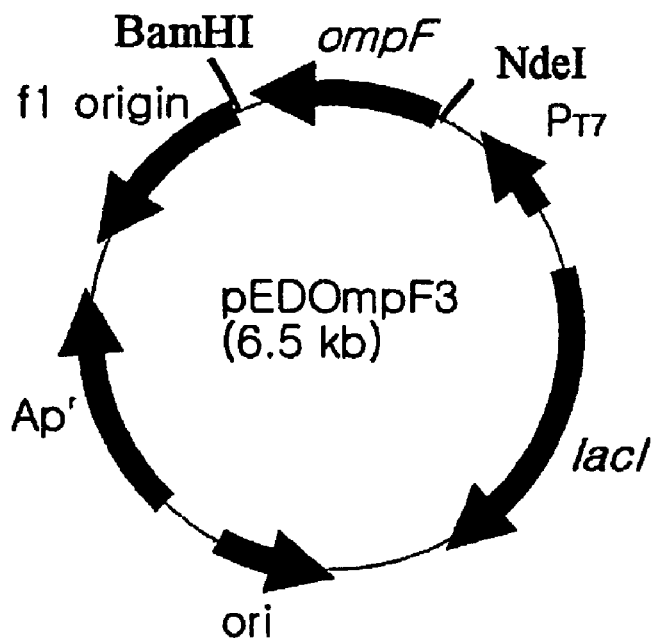
FIG. 4 represents a genetic map of the recombinant expression vector pEDOmpF3.

First, an expression vector of ompF gene was constructed employing T7 promoter that is a strong inducible expression promoter. PCR was performed using genomic DNA of E. coli BL21(DE3) as a template and primer 4 and primer 10: 5'-GC-GAATTCATATGATGAAGCGCAATATTCTG-3'(SEQ ID NO. 10). The amplified PCR product was digested by NdeI and BamHI and cloned into an expression vector pET21c (Novagen, U.S.A.) to construct a recombinant expression vector pEDOmpF3. *E. coli* XL1-Blue strain was transformed with pEDOmpF3 and the recombinant expression vector pEDOmpF3 was obtained therefrom(see: FIG. 4). FIG. 4 represents a genetic map of recombinant expression vector pEDOmpF3.

Figure 5:
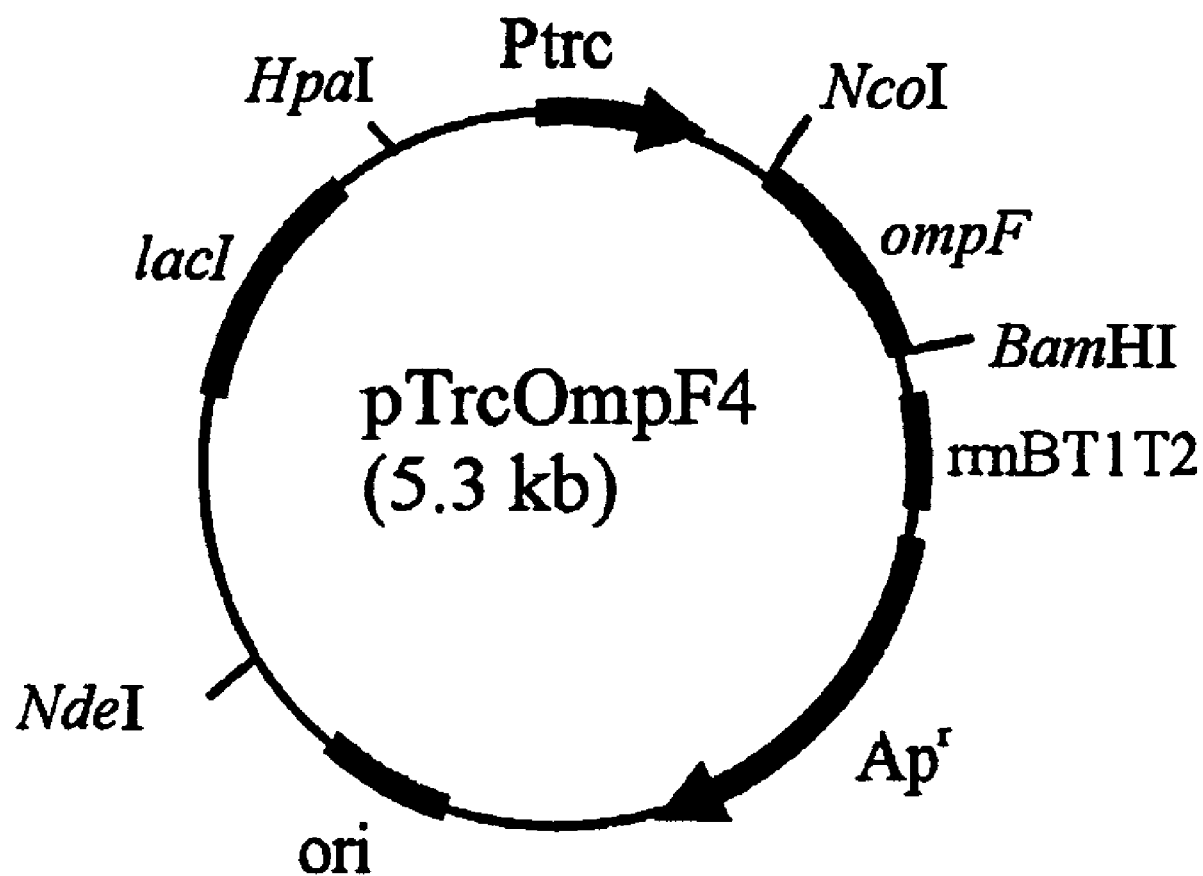
FIG. 5 represents a genetic map of the recombinant expression vector pTrcOmpF4.

Secondly, an expression vector of ompF gene was constructed employing Trc promoter that is an inducible expression promoter. PCR was performed using genomic DNA of *E. coli* BL21(DE3) strain as a template and primer 4 and primer 11: 5'-GCGAATTCCATGGTGAAGCGCAATAT-TCTGGCAG-3'(SEQ ID NO. 11). The amplified PCR product was digested by NdeI and BamHI and cloned into an expression vector pTrc99A to construct a recombinant expression vector pTrcOmpF4. *E. coli* XL1-Blue strain was transformed with pTrcOmpF4 and the recombinant expression vector pTrcOmpF4 was obtained therefrom(see: FIG. 5). FIG. 5 represents a genetic map of recombinant expression vector pTrcOmpF4.

Thirdly, an expression vector pOmpF6 comprising OmpF promoter constructed in Example 2 was used as an expression vector of ompF gene.

The said three recombinant expression vectors(pEDOmpF3, pTrcOmpF4 and pOmpF6) were used to transform *E. coli* BL101 strain prepared in Example 2. Transformed recombinant strains were screened on LB plate containing ampicillin and kanamycin. In order to select the most efficient secretion system that produces OmpF proteins on the cell surface, each transformed recombinant *E. coli* was cultured in 50 mL of R/2 media{$(NH_4)_2HPO_4$ 2 g/L, $KH_2PO_4$ 6.75 g/L, citric acid 0.85 g/L, $MgSO_4.7H_2O$ 0.7 g/L, 5M HCl/L, $FeSO_4.7H_2O$ 10 g/L, $ZnSO_4.7H_2O$ 2.25 g/L, $CuSO_4.5H_2O$ 1 g/L, $MnSO_4.5H_2O$ 0.5 g/L, $Na_2B_4O_7.10H_2O$ 0.23 g/L, $CaCl_2.2H_2O$ 2 g/L, $(NH_4)_6MO_7O_{24}$ 0.1 g/L glucose 10 g/L} at a temperature of 37° C.

1M IPTG(isopropyl-β-thiogalactoside, final concentration) was added to induce expression of ompF gene when $O.D._{600}$ of culture of the transformant harbouring pEDOmpF3 and pTrcOmpF4 reached at 0.7. *E. coli* BL21 (DE3) and *E. coli* BL101 were also cultured under the same condition for the control group. Outer membrane protein fractions were prepared from the culture of each strain by the method described in Example 1, and analysed by SDS-PAGE to compare expression levels of OmpF protein. *E. coli* BL101 transformed with pOmpF6 vector produced and accumulated OmpF protein in the outer membrane whose expression level was similar to that of *E. coli* BL21(DE3), a parent strain. From the said results, it was clearly demonstrated that OmpF promoter is the most preferred for the expression of OmpF-fused protein.

The present inventors designated *E. coli* BL101 transformed with a recombinant expression vector pOmpF6 as "*Escherichia coli* BL101/pOmpF6", and deposited with the Korean Collection for Type Cultures(KCTC, #52 Oun-dong, Yusong-ku, Taejon 305-333, Republic of Korea), an international depository authority, as Accession No. KCTC 1026BP on Jun. 1, 2001.

EXAMPLE 4

Construction of OmpF-β-endorphin Expression Vector

Figure 6:
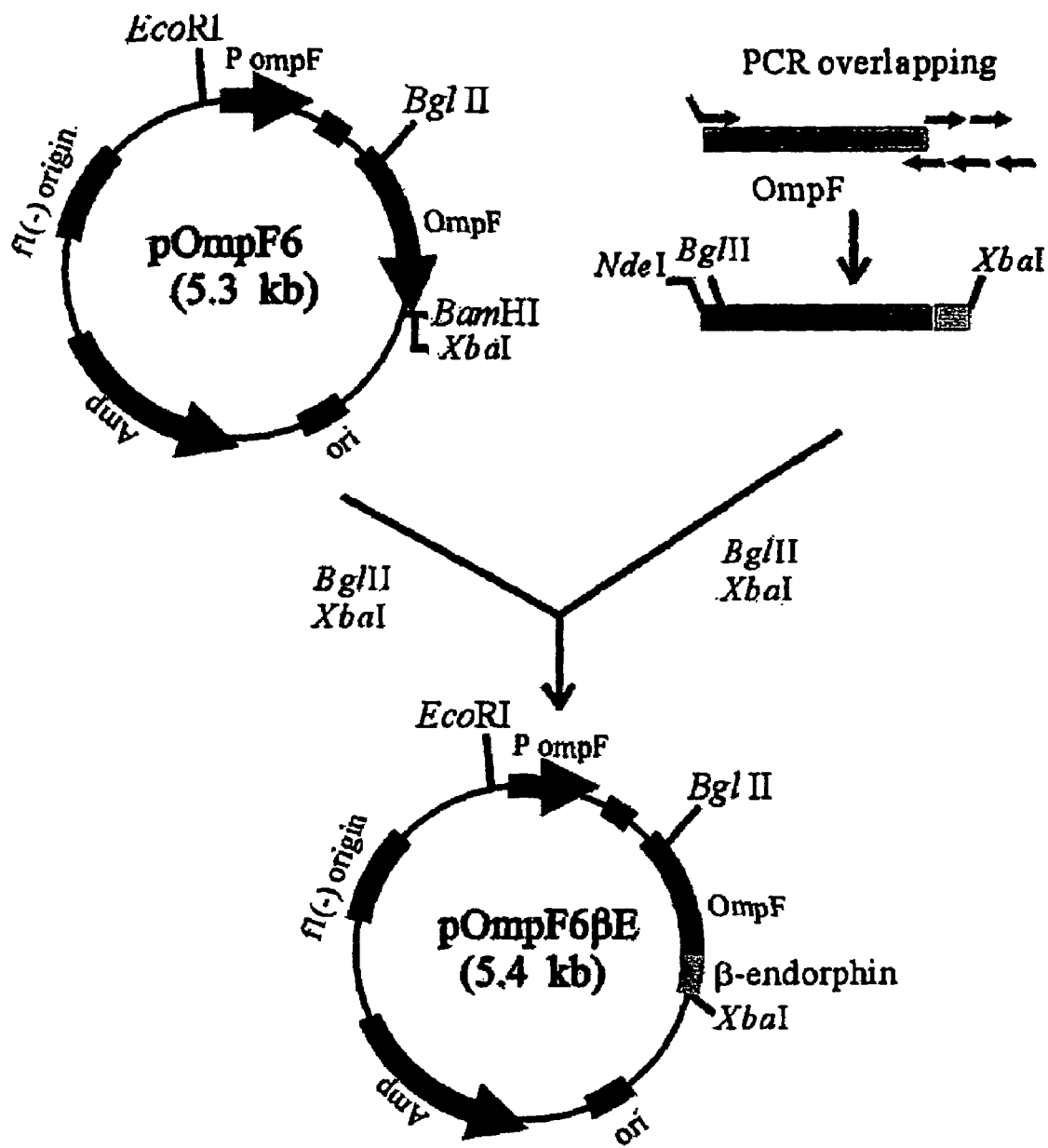
FIG. 6 represents a construction scheme and a genetic map of recombinant expression vector pOmpF6βE.

Beta endorphin protein (β endorphin) consists of 31 amino acids, and gene encoding β-endorphin consists of 93 nucleotides(see: Takahashi H. et al., FEBS Lett., 135:97-102, 1981). To prepare the gene coding for β-endorphin, primer 12: 5'-ACCGCCATACCTTCCCTCGATGAACTGG-TAAACGATA-3'(SEQ ID NO. 12), primer 13: 5'-GGAAG-GTATGGCGGTTTCATGACCAGC-GAAAAAAGCCAGAC-3'(SEQ ID NO. 13), primer 14: 5'-CGCGTTTTTAAACAGGGTCAC-CAGCGGGGTCTGGCTTTTTTCGC-3'(SEQ ID NO. 14), primer 15: 5'-CCCTGTTTAAAAACGCGATCAT-CAAAAACGCGTATAAAAAAG-3'(SEQ ID NO. 15), and primer 16: 5'-GCGGATCCCTATTATTCGCCTTTTT-TATACGCGTTTTTG-3'(SEQ ID NO. 16) were synthesized, respectively, and used for PCR. PCR was also performed using genomic DNA of *E. coli* BL21(DE3) as a template and primer 10 and primer 12 as primers. Both DNA fragments amplified by the above PCRs were mixed with primer 10 and primer 16, and then PCR was performed again to obtain PCR fragments containing a gene encoding four amino acids which is recognized and cleaved by Factor Xa, and β-endorphin gene fused with ompF gene. The said PCR fragments were digested with BglII and XbaI and ligated into an expression vector pOmpF6 to construct a recombinant expression vector pOmpF6βE. *E. coli* XL1-Blue strain was transformed with pOmpF6βE and the recombinant expression vector pOmpF6βE was obtained therefrom(FIG. 6). FIG. 6 represents a construction scheme and a genetic map of a recombinant expression vector pOmpF6βE. The nucleotide sequence of β-endorphin gene fused with ompF gene in the recombinant expression vector pOmpF6βE is 5'-TATGGCG-GTTTCATGACCAGCGAAAAAAGCCAGAC-CCCGCTGGTGACCCTGTTTAAAAACGCGATCATCAA AAACGCGTATAAAAAAGGCGAATAA-3'(SEQ ID NO. 18), which expresses Tyr Gly Gly Phe Met Ala Ser Glu Lys Ser Gln Ala Pro Leu Val Ala Leu Phe Lys Asn Ala Ile Ile Lys Asn Ala Tyr Lys Lys Gly Glu Stop(SEQ ID NO. 17).

*E. coli* BL101 strain was transformed with the recombinant expression vector pOmpF62E and transformants were screened on LB plate containing ampicillin and kanamycin.

EXAMPLE 5

Extracellular Production of OmpF-β-endorphin Fusion Protein

*E. coli* transformant prepared in Example 4 was inoculated into 1.8 L of R/2 media and cultured at 37° C. by fed-batch culture. The substrate was consisted of glucose 700 g/L and $MgSO_4.7H_2O$ 20 g/L, and fed into culture media at a speed of 10 mL/min to keep glucose concentration at 0.7 g/L if pH of culture media increased above 6.88, and air and oxygen were supplied automatically to keep dissolved oxygen at 40% (v/v). After 17.5 hours of culture, optical density at 600 nm of the culture was measured as 150.5 and dry weight of cells was 54.1 g/L. To measure the amount of fusion proteins, culture media collected at regular intervals were centrifuged, and the supernatants were analysed by electrophoresis, which showed that OmpF-β-endorphin fusion protein of 40 kDa was accumulated in culture media and the accumulated amount of OmpF-β-endorphin fusion protein was increased depending on the culture time. Final amount of OmpF-β-endorphin fusion protein was 4.64 g/L, which corresponded to 45% of total proteins in the culture media.

EXAMPLE 6

Purification of β-endorphin Produced Extracellularly

OmpF-β-endorphin fusion protein accumulated in the culture media in Example 5 was purified: First, 50 mL of culture media was centrifuged to remove bacterial cells. Then, OmpF-β-endorphin fusion protein was purified from the supernatant by anion-exchange chromatography, where Q2-column(BIO-RAD Co., U.S.A.) was used as anion-exchange resin and 50 mM Tri-HCl(pH 7.0) buffer solution was used as mobile phase and flow rate was 1 mL/min. OmpF-β-endorphin fusion proteins were eluted with a linear gradient of 0 to 1 M NaCl. Total amount of OmpF-β-endorphin fusion proteins eluted at 0.45M of NaCl was 89.1 mg. NaCl was removed from OmpF-β-endorphin fusion proteins by dialysis. In order to remove OmpF protein from OmpF-β-endorphin fusion protein, Factor Xa and OmpF-β-endorphin fusion protein were mixed at a ratio of 1 :200(w/w) and incubated at 23° C. for 12 hours. Then, β-endorphin protein was purified by reverse-phase HPLC, where Microsorb-MV $C_{18}$ column (4.6×250 mm, Varian, U.S.A.) was used as HPLC column and 0.1% (v/v) TFA(trifluoroacetic acid) solution was used as mobile phase and flow rate was 1 mL/min. Elution of proteins was monitored at 280 nm with a UV detector(see: Table 1).

TABLE 1

Purification of β-endorphin

| Purification Step | Volume (mL) | Total Protein (mg) | Fusion Protein (mg) | β-endorphin (mg) | Yield (%) | Purity (%) |
|---|---|---|---|---|---|---|
| Culture Medium | 50 | 515 | 232 | 20.3 | 100 | 3.9 |
| Anion-exchange Resin | 63 | 118.8 | 89.1 | 7.8 | 38.4 | 5.9 |
| RP-HPLC | 12 | 2.8 | — | 2.8 | 13.8 | >99 |

As shown in Table 1 above, 2.8 mg of β-endorphin was purified by the technique of HPLC. Further, N-terminal sequencing of purified β-endorphin revealed that the amino acid sequence is Tyr-Gly-Gly-Phe-Met-Thr-Ser-Glu-Lys (SEQ ID NO: 21), which corresponds with N-terminal amino acids of β-endorphin.

As clearly illustrated and demonstrated as above, the present invention provides an expression vector comprising genes encoding OmpF and desired protein, *E. coli* transformed with the expression vector, and a method for extracellular production of desired proteins by employing the same. The recombinant expression vector of the invention comprises ampicillin-resistant gene, OmpF promoter and OmpF gene. In accordance with the invention, a desired protein can be produced extracellularly by simpler method than conventional methods in a manner that: secretory production of OmpF fusion protein begins simultaneously with growth of cells through constitutive expression employing OmpF promoter, and as the concentration of cells increases, the amount of secretory production of the protein also increases continuously. Therefore, desired proteins can be produced in large quantities by a high concentration culture of cells.

While the present invention has been shown and described with reference to particular embodiments, it will be apparent to those skilled in the art that certain changes and modifications can be made to this invention without departing from the spirit or scope of the invention as it is set forth herein.

What is claimed is:

1. An expression vector comprising:
   an OmpF promoter;
   an OmpF gene encoding an OmpF protein:
   a cleavage-site gene encoding an RNA or protein cleavage site; and
   a gene of interest encoding a protein of interest,
   wherein the expression vector encodes a fusion protein comprising the OmpF protein, the cleavage site and the protein of interest, and wherein the cleavage-site gene is located between the OmpF gene and the gene of interest in the expression vector such that the RNA or protein cleavage site is located between the OmpF protein and the protein of interest in the fusion protein.

2. The expression vector of claim 1, further comprising a selectable marker.

3. The expression vector of claim 1, wherein said selectable marker is ampicillin resistance.

4. The expression vector of claim 1, wherein said cleavage site is configured to be cleaved by an RNase or a protease.

5. The expression vector of claim 4, wherein said protease is selected from the group consisting of: Factor Xa, enterokinase, IgA protease, intein, genenase, thrombin, trypsin, pepsin, subtilisin, and plasmin.

6. The expression vector of claim 1, wherein said protein of interest is selected from the group consisting of: a polypeptide, a protein, an enzyme, or an antibody.

7. The expression vector of claim 6, wherein said protein of interest is an amino acid sequence comprising SEQ ID NO:17.

8. The expression vector of claim 1, wherein said expression vector is pOmpF6 contained in the deposition made under accession number KCTC 1026BP.

9. The expression vector of claim 1, wherein said OmpF gene comprises the signal sequence.

10. A microorganism transformed with the expression vector of claim 1.

11. The microorganism of claim 10, wherein said microorganism is *Escherichia* sp.

12. The microorganism of claim 10, wherein said microorganism is *Salmonella* sp.

13. The microorganism of claim 10, wherein said microorganism lacks the OmpF gene other than the OmpF gene comprised within the expression vector.

14. The microorganism of claim 10, wherein said microorganism is *E. coli* BL101/pOmpF6 deposited under accession number KCTC 1026BP.

15. A method for the production of a protein of interest, comprising:
    providing a microorganism transformed with the expression vector of claim 1;
    culturing the microorganism in a culture medium, thereby producing the fusion protein in the medium; and
    separating the fusion protein from the medium.

16. The method of claim 15, wherein the microorganism does not express OmpF protein in the absence of the expression vector.

17. The method of claim 15, wherein the microorganism is *Escherichia* sp. or *Salmonella* sp.

18. The method of claim 17, wherein the *Escherichia* sp. is *E coli*.

19. The method of claim 15, wherein the microorganism is *E. coli* BL101/pOmpF6 deposited under accession number KCTC 1026BP.

20. The method of claim 15, further comprising cleaving the fusion protein at the cleavage site using an enzyme configured to selectively cleave the cleavage site after separating the fusion protein from the medium.

21. The method of claim 20 wherein the enzyme is an RNase or protease.

22. The method of claim 21 wherein the protease is selected from the group consisting of: Factor Xa, enterokinase, genenase, IgA protease, intein, thrombin, trypsin, pepsin, subtilisin, and plasmin.

23. The method of claim 15, further comprising removing the microorganism from the medium after producing the fusion protein in the medium.

24. The method of claim 15, wherein said separating of the fusion protein from the medium comprises using anion-exchange chromatography.

25. The method of claim 20 further comprising collecting the protein of interest cleaved from the fusion protein after cleaving the fusion protein.

26. The method of claim 25 wherein said collecting of the protein of interest comprises using reverse-phase HPLC.

* * * * *

SEQUENCE LISTING

```
<160> NUMBER OF SEQ ID NOS: 18

<210> SEQ ID NO 1
<211> LENGTH: 37
<212> TYPE: DNA
<213> ORGANISM: Artificial Sequence
<220> FEATURE:
<223> OTHER INFORMATION: primer

<400> SEQUENCE: 1
cgcgccatgg atattaatac tgaaactgag atcaagc                              37

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
cgggatcctc atcgccattg ctccccaaat ac                                   32

<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3
```

-continued cggaattctg gattataccg acgcag     26

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
gcggatcctt agaactggta aacgatac     28

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
cgctgcagtt agaaaaactc atcgagcatc     30

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
gcctgcaggc cacgttgtgt cctcaaa     27

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
ccacagcaac ggtgtcgtct g     21

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
gatcggaatt gatttgagtt tcc     23

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
atctttatct ttgtagcact ttcac     25

<210> SEQ ID NO 10
<211> LENGTH: 31
<212> TYPE: DNA
<213> ORGANISM: Artificial Sequence

```
<220> FEATURE:
<223> OTHER INFORMATION: primer

<400> SEQUENCE: 10
gcgaattcat atgatgaagc gcaatattct g                              31

<210> SEQ ID NO 11
<211> LENGTH: 34
<212> TYPE: DNA
<213> ORGANISM: Artificial Sequence
<220> FEATURE:
<223> OTHER INFORMATION: primer

<400> SEQUENCE: 11
gcgaattcca tggtgaagcg caatattctg gcag                           34

<210> SEQ ID NO 12
<211> LENGTH: 37
<212> TYPE: DNA
<213> ORGANISM: Artificial Sequence
<220> FEATURE:
<223> OTHER INFORMATION: primer

<400> SEQUENCE: 12
accgccatac cttccctcga tgaactggta aacgata                        37

<210> SEQ ID NO 13
<211> LENGTH: 41
<212> TYPE: DNA
<213> ORGANISM: Artificial Sequence
<220> FEATURE:
<223> OTHER INFORMATION: primer

<400> SEQUENCE: 13
ggaaggtatg gcggtttcat gaccagcgaa aaaagccaga c                   41

<210> SEQ ID NO 14
<211> LENGTH: 44
<212> TYPE: DNA
<213> ORGANISM: Artificial Sequence
<220> FEATURE:
<223> OTHER INFORMATION: primer

<400> SEQUENCE: 14
cgcgttttta aacagggtca ccagcggggt ctggcttttt tcgc                44

<210> SEQ ID NO 15
<211> LENGTH: 42
<212> TYPE: DNA
<213> ORGANISM: Artificial Sequence
<220> FEATURE:
<223> OTHER INFORMATION: primer

<400> SEQUENCE: 15
ccctgtttaa aaacgcgatc atcaaaaacg cgtataaaaa ag                  42

<210> SEQ ID NO 16
<211> LENGTH: 39
<212> TYPE: DNA
<213> ORGANISM: Artificial Sequence
<220> FEATURE:
<223> OTHER INFORMATION: primer

<400> SEQUENCE: 16
gcggatccct attattcgcc ttttttatac gcgttttg                       39
```

```
<210> SEQ ID NO 17
<211> LENGTH: 31
<212> TYPE: PRT
<213> ORGANISM: Artificial Sequence
<220> FEATURE:
<223> OTHER INFORMATION: Fusion Protein

<400> SEQUENCE: 17

Tyr Gly Gly Phe Met Thr Ser Glu Lys Ser Gln Thr Pro Leu Val Thr
 1               5                  10                  15

Leu Phe Lys Asn Ala Ile Ile Lys Asn Ala Tyr Lys Lys Gly Glu
            20                  25                  30

<210> SEQ ID NO 18
<211> LENGTH: 96
<212> TYPE: DNA
<213> ORGANISM: Artificial Sequence
<220> FEATURE:
<223> OTHER INFORMATION: fusion protein cDNA

<400> SEQUENCE: 18 tatgcggtt tcatgaccag cgaaaaaagc cagaccccgc tggtgaccct gtttaaaaac      60
gcgatcatca aaacgcgta taaaaaaggc gaataa                               96
```